United States Patent
Trubetskoy et al.

(10) Patent No.: US 6,319,678 B1
(45) Date of Patent: *Nov. 20, 2001

(54) PROCESS FOR GLUCURONIDATION SCREENING

(75) Inventors: Olga Trubetskoy, Middleton, WI (US); Peter M. Shaw, Yardley, PA (US)

(73) Assignee: PanVera Corporation, Madison, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/344,995

(22) Filed: Jun. 25, 1999

Related U.S. Application Data

(60) Provisional application No. 60/090,727, filed on Jun. 26, 1998.

(51) Int. Cl.[7] .............................. C12Q 1/48; C12Q 1/00; C12Q 1/54
(52) U.S. Cl. ................................. 435/15; 435/18; 435/14; 435/4
(58) Field of Search .................................. 435/15, 18, 14, 435/4

(56) References Cited

U.S. PATENT DOCUMENTS 5,603,917 * 2/1997 Tweedle et al. .................... 436/173

OTHER PUBLICATIONS

Bansal, S. et al., :A Unifed Method for the Assay of Uridine Diphosphoglucuronylltransferase Activities Toward Various Aglycones Using Uridine Diphospho (U–14C)Glucuronic Acid. *Analytical Biochemistry.* 1980; 109; 321–329.

Crespi, C. Et al., "Microtiter Plate Assays for Inhibition of Human, Drug–Metabolizing Cytochromes P450." *Analytical Biochemistry.* 1997; 248; 188–190.

DiMarco, M.P. Et al., "On–line Deconjugation of Glucuronides Using an Immobilized Enzyme Reactor Based Upon B–Glucuronidase." *Journal of Chromatography B.* 1998; 715; 379–386.

Ethell, B. Et al., "a Universal Radiochemical High–Performance Liquid Chromatographic Assay for the Determination of UDP–Glucuronosyltransferase Activity."*Analytical Biochemistry.* 1998;225; 142–147.

Hawes, Edward., "1996 ASPET N–Glucuronidation of Xenobiotics Symposium." *Drug Metabolism and Disposition.* 1998; vol. 26, No. 9; 830–837.

Heidrun, M. Et al., "Radioassay of UDP–Glucuronosyltransferase Activities Toward Endogenous Substrates Using Labled UDP–Glucuronic Acid and an Organic Solvent Extraction Procedure," *Analytical Biochemistry.* 1994; 219; 182–188.

January 1999; (PSTT vol. 2(1) p. 13–19).

Pritchard, M. Et al., "A Method for the Determination of UDP–Glucuronosyltransferase Activity Toward Arylcarboxylic Acids." *Analytical Biochemistry.* 1993; 212; 487–497.

Sperker,B. Et al., "High–Performance Liquids Chromatographic Quantification of 4–Methylumbellifryl–B–D–Glucuronide As a Probe for Human B–Glucuronidase Activity in Tissue Homogenates." *Journal of Chromatography B.* 1996; 685; 181–184.

Woo, L. Et al., "Active Site Directed Inhibition of Estrone Sulfatase by Nonsteroidal Coumarin Sulfamats." *J. Med. Chem.* 1996; 39, 1349–1351.

* cited by examiner

Primary Examiner—Louise N. Leary
(74) Attorney, Agent, or Firm—Mark K. Johnson

(57) ABSTRACT

A process used to identify activity of conjugative enzymes involved in xenobiotic transformations, such as glucuronosyltransferases.

1 Claim, 5 Drawing Sheets

- 4-methylumbelliferyl-β-glucuronide, 5 μM
- 4-methylumbelliferyl-β-glucuronide, 20 μM
- 4-methylumbelliferyl-β-glucuronide, 100 μM

PROCESS FOR GLUCURONIDATION SCREENING

CROSS-REFERENCE TO RELATED APPLICATIONS

Provisional Application Ser. No. 60/090,727.
Filing Date Jun. 26, 1998.

FEDERALLY SPONSORED RESEARCH

N/A.

FIELD

The field of this invention relates to a process for screening for enzymes activity. More particularly the process is a method that can be used to identify activity of glucuronosyltransferases.

BACKGROUND

Drug metabolism problems such as production of toxic metabolites and unfavorable pharmacokinetics cause almost half of all drug candidate failures during clinical trials. Although glucuronidation is one of the most important routes of biotransformation, the broad and overlapping substrate specificity of the hepatic UDP-glucuronosyltransferases (UGTs) that catalyze glucuronidation remains poorly understood. The two main reasons for this situation are the lack of isolated individual UGT isozymes and the lack of assay methods suitable for detecting glucuronidation of diverse chemicals.

The UDP-glucuronosyltransferases are a family of enzymes that catalyze the glucuronidation of endogenous and xenobiotic chemicals (Equation 1), generating products that are more hydrophilic and thus more readily excreted in bile or urine.
Equation 1
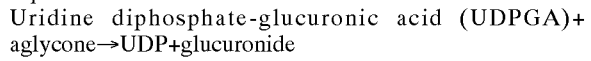
Uridine diphosphate-glucuronic acid (UDPGA)+ aglycone→UDP+glucuronide The UGTs play a key role in several important metabolic functions, including:

elimination of drugs such as non-steroidal anti-inflammatories, opioids, antihistamines, antipsychotics and antidepressants, detoxification of environmental contaminants such as benzo(a)pyrenes, regulation of hormone levels for androgens, estrogens, progestins, and retinoids, elimination of the heme degradation product bilirubin.

Although glucuronidation generally is classified as Phase II metabolism—the phase occurring after P450 dependent oxidative metabolism—many compounds do not require prior oxidation because they already possess functional groups that can be glucuronidated. Examples of first pass metabolism catalyzed by UGTs include the UGT2B7-dependent glucuronidation of morphine and the glucuronidation of 5-lipoxygenase inhibitors (antiinflammatories); in the latter case glucuronidation was demonstrated to be the rate limiting step for in vivo plasma clearance.

Notably, glucuronidation does not always cause decreased biological activity and/or detoxification. Glucuronides of some drugs are toxic, and have been linked with adverse drug reactions including immune hypersensitivity. Glucuronidation can modulate the potency of some drugs: the 6-glucuronide of morphine is a more potent analgesic than the parent compound, whereas the 3-glucuronide is a morphine antagonist. In addition, steroid glucuronidation can produce more active or toxic metabolites under pathophysiological conditions or during steroid therapies.

UGTs are 50–60 kDa integral membrane proteins with the major portion of the protein, including the catalytic domain, located in the lumen of the endoplasmic reticulum and a C-terminal anchoring region spanning the ER membrane. Two UGT families—UGT1 and UGT2—have been identified in humans; although the members of these families are less than 50% identical in primary amino acid sequence, they exhibit significant overlap in substrate specificity.

The members of the UGT1 family that are expressed in human liver, where the majority of xenobiotic metabolism takes place, include UGT 1A1, 1A3, 1A4, 1A6, and 1A9. Although the UGT2 family has not been studied as extensively, it is known that UGT2B4, 2B7, 2B10, 2B15 and 2B17 are expressed in the liver. Mutations in UGTs are known to have deleterious effects, including hyperbilirubinaemia which occurs with a frequency of 5–12% and can lead to neurotoxicity and in severe cases, death. As is the case for other drug metabolizing enzymes such as P450s, interindividual differences in UGT expression levels have been observed and linked to differences in drug responses (17,18). For instance, low expression of UGT1A1, as in patients with Gilbert's syndrome, has been associated with the toxicity of Irinotecan, a promising anticancer agent. In addition, UGT upregulation in tumor tissues has been identified as a possible cause of anticancer drug resistance (20,21).

Specificity for Aglycones—UGT substrates are known as aglycones; the products of the reaction are called glucuronides. All of the known UGTs exhibit broad substrate specificity, with a single isozyme catalyzing glucuronidation of a broad range of structurally unrelated compounds; not surprisingly there also is a great deal of overlap in the specificities of UGT isozymes. The sites of glucuronidation generally are nucleophilic nitrogen, sulfur or oxygen atoms in functional groups such as aliphatic alcohols, phenols, carboxylic acids, primary through tertiary amines, and free sulfyhydryls. The aglycone binding site is believed to be in the N-terminal portion of the UGT polypeptide, the region of the protein that shows the greatest variability in sequence among isozymes. However, efforts to define the aglycone binding site by correlating N-terminal amino acid sequences of UGT isozymes with their substrate specificities have been unsuccessful.

Despite their broad substrate specificities, UGTs can be highly regio- and stereo-selective. It has been suggested that substrates bind loosely to a very "open" substrate binding pocket—as with some P450s—and rotate until reactive functional groups are suitably oriented to the bound UDPGA and the amino acids involved in catalysis. Although several studies on the substrate specificities of individual recombinant UGTs have been performed, most have been limited to a relatively small number of compounds within one or two structural classes.

HTS assay methods described herein can be used to rapidly screen large numbers of diverse chemicals thus allowing a systematic effort to fully define the "chemical space" recognized by each of the key hepatic UGTs. Moreover, these HTS assay methods will fulfill the immediate needs of the pharmaceutical industry by providing a means to screen large numbers of diverse compounds for glucuronidation with a panel of the key human UGT isozymes. The information obtained with these HTS assays can be used in the following ways:

After isozyme identification, more detailed kinetic studies with the appropriate UGT isozyme can be used to predict in vivo clearance rates, reducing the number of compounds that fail in clinical studies due to poor pharmacokinetics.

Knowledge of metabolism by a specific UGT alerts the drug discovery team to potential pharmacogenetic problems, since genetic differences in UGT levels are recognized as an important factor in varying responses to therapeutics.

Identification of the UGT responsible for the metabolism of a drug will aid in judicious selection of the in vitro assays or animal models used for preclinical assessment of possible drug—drug interactions and toxicology testing, thereby reducing inappropriate or unnecessary use of animals for experiments.

Metabolism data can be used as a component of rational drug design. A better understanding of the structure-activity relationships that define substrate specificity for the various UGT isozymes would provide a basis for structural modifications of primary compounds to change their metabolism profile. This approach was used successfully for development of ABT-761, a 5-lipoxygenase inhibitor.

The testing of glucuronidated compounds can lead to the discovery of valuable prodrugs that are inactive until metabolized in the body into an active form.

To confirm the need for improved technology to probe the specificity of UGT isozymes, it is useful to review the methods currently employed for in vitro drug metabolism studies, and the reasons why they are not adequate for immediate drug discovery needs.

Sources of UGTs. The important drug metabolizing UGT isozymes are located in the endoplasmic reticulum of liver cells. Natural sources of UGT for in vitro assays include liver slices, cultured cells, and cell fractions such as human liver microsomes. The major drawbacks of these unpurified systems are that they contain a mixture of multiple UGT isozymes and other drug metabolizing enzymes. As a result, they are of limited use in obtaining meaningful data on a specific UGT isozyme—particularly in an HTS format. Heterologous expression systems such as mammalian and BaV-infected insect cells have made it possible to produce large amounts of microsomal membranes highly enriched in a single UGT isozyme.

Assay methods. UGTs generally are assayed by isolation and quantification of the radioactively labeled metabolites produced from the parent compound in reactions containing radiolabeled UDPGA. In most cases, this involves chromatographic techniques such as thin layer chromatography (TLC) or high pressure liquid chromatography (HPLC), and in some cases phase separations. There are two major drawbacks to these assays methods. First, the need to isolate the reaction products makes the methods too cumbersome and time consuming for use in any type of high volume assay format. Second, different glucuronidated metabolites have different chromatographic properties, raising an obvious technical barrier to screening diverse compounds for metabolism by a panel of isolated UGT isozymes. For some substrates, products and reactants can be differentiated on the basis of altered absorbance or fluorescence after glucuronidation, however, these methods are limited to a few UGT isozymes.

and control (unshaded bars) incubations, which include α-naphthol, is shown.

SUMMARY

We have developed a universal HTS activity assay that enables screening for glucuronidation of large numbers of diverse chemicals by any isolated recombinant UGT using a single detection method. The method is based upon glucuronides, the products of UGT reactions, inhibiting the formation of a fluorescent product by a bacterial b-glucuronidase. The method is non-radioactive, homogenous and can be used for identification of novel UGT substrates and inhibitors in a high throughput screening (HTS) format. UGT assay methods are based on inhibition of a fluorescent b-glucuronidase reporter reaction. This approach provides the following advantages over existing methods:

Universal Assay Method. The assay method will apply for all UGT isozymes and for all aglycone substrates, thus making it ideal for screening large numbers of diverse compounds.

Nonradioactive. The assay will not employ radioisotopes, thus eliminating the hazards and regulatory and handling costs associated with such agents.

Homogeneous Assay Method. The assay will be homogenous, eliminating separation steps and possibly allowing continuous monitoring of reaction rate, in turn allowing more flexibility for kinetic analyses.

The novel HTS assay method will allow investigators to survey the full range of potential substrate specificity for the key hepatic UGT isozymes.

Assay Principle: Cleavage of 4-methylumbelliferyl b-D-glucuronide by bacterial b-glucuronidase generates the highly fluorescent compound, 4-methylumbelliferone. Diverse b-D-glucuronides act as competitors of b-glucuronidase, thus providing the basis of a coupled assay method for detection of glucuronide production by recombinant UGT isozymes. Using human recombinant human UGT 1A6 as an example, we demonstrate the feasibility of using this coupled assay method for fluorescence detection of UGT activity with several structurally diverse substrates. The 4-methylumbelliferyl b-D-glucuronide cleavage assay can easily be adapted to high throughput formats to detect the presence of b-D glucuronides generated using recombinant glycosyl transferase preparations.

Methods

Methods are included in text and figure legends. b-D-glucuronidase (Part G-7396), α-napthyl b-D-glucuronide, b-trifluoromethylumbelliferyl b-D-glucuronide, b-estradiol 3-(b-D-glucuronide), p-acetominophenyl b-D-glucuronide, 5 □-androstane-3α, 17α-diol-11-one-17-carboxilic acid-3-(b-D-glucuronide), UDPGA and 4-methylumbelliferone b-D-glucuronide were obtained from Sigma, St. Louis Mo. Tetrahydrocortisone 3-b-D-glucuronide was obtained from Molecular Probes, Eugene, Oreg. Recombinant control and UGT1A6 membrane preparations were generated at PanVera Corporation and are commercially available from PanVera, Madison Wis. All other reagents were analytical grade or better and purchased from a variety of commercial sources.

Results and Discussion

Figure 1A:
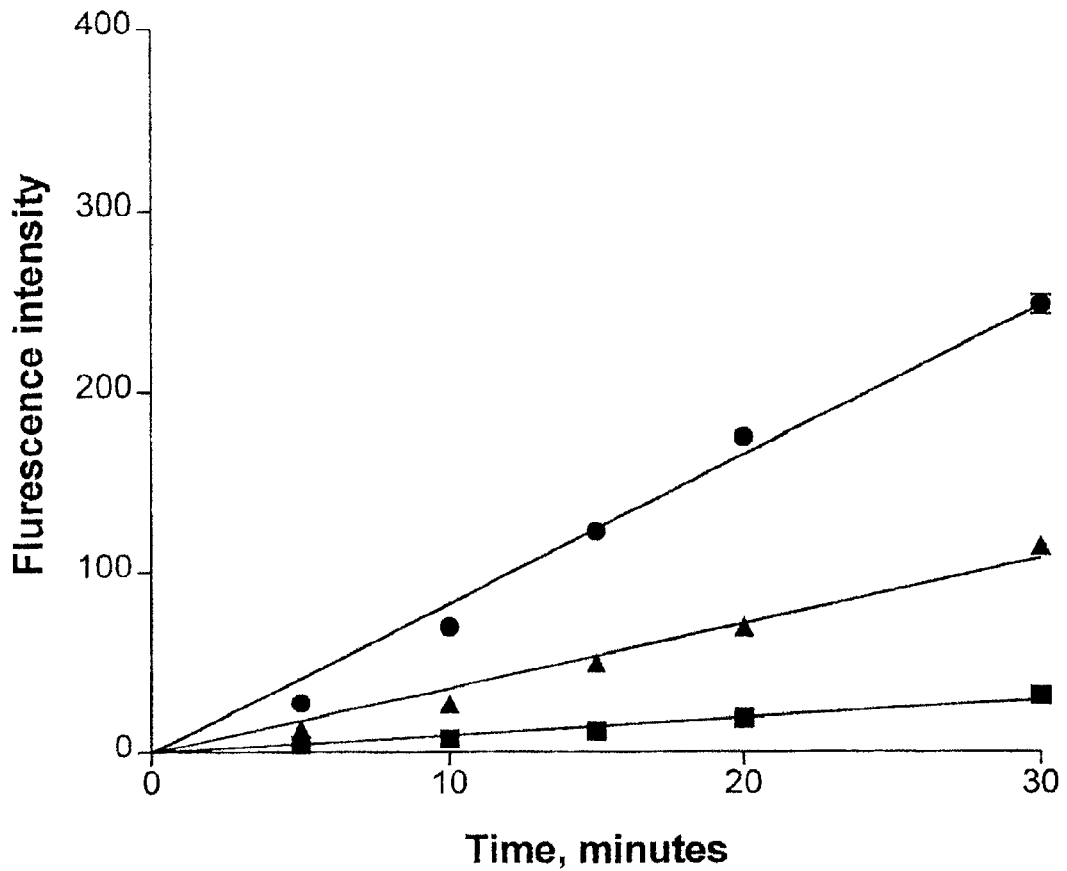
FIG. 1 Kinetic measurements of 4-methylumbelliferylb-D-glucuronide cleavage by b-gluuronidase. In part A, 100 µl assays were performed in triplicate using 100 mM Tris-HCl buffer, pH 7.4, containing 10 mM $MgCl_2$, 0.1 µg/ml b-gluuronidase and 5 (■), 20 (▲), and 100 (●) µM, 4-methylumbelliferyl-b-D-glucuronide. Reactions were started by the addition of enzyme, incubated for indicated times at ambient temperature and then quenched with 100 µl of 0.1 M $Na_2CO_3$, pH 9.5, containing 0.1% CHAPS. Fluorescence intensity was measured with a Beacon fluorescent polarization instrument (PanVera Corporation, Madison, Wis.) in intensity mode, using excitation and emission filters of 360 nm and 440 nm, respectively, and slit widths set at 10 nm. Part B, assays were performed in duplicate for 20 min as above with the indicated amount of 4-methylumbelliferyl-b-D-glucuronide. 4-Methyumbelliferone concentration was determined from a calibration curve.
Figure 1B:
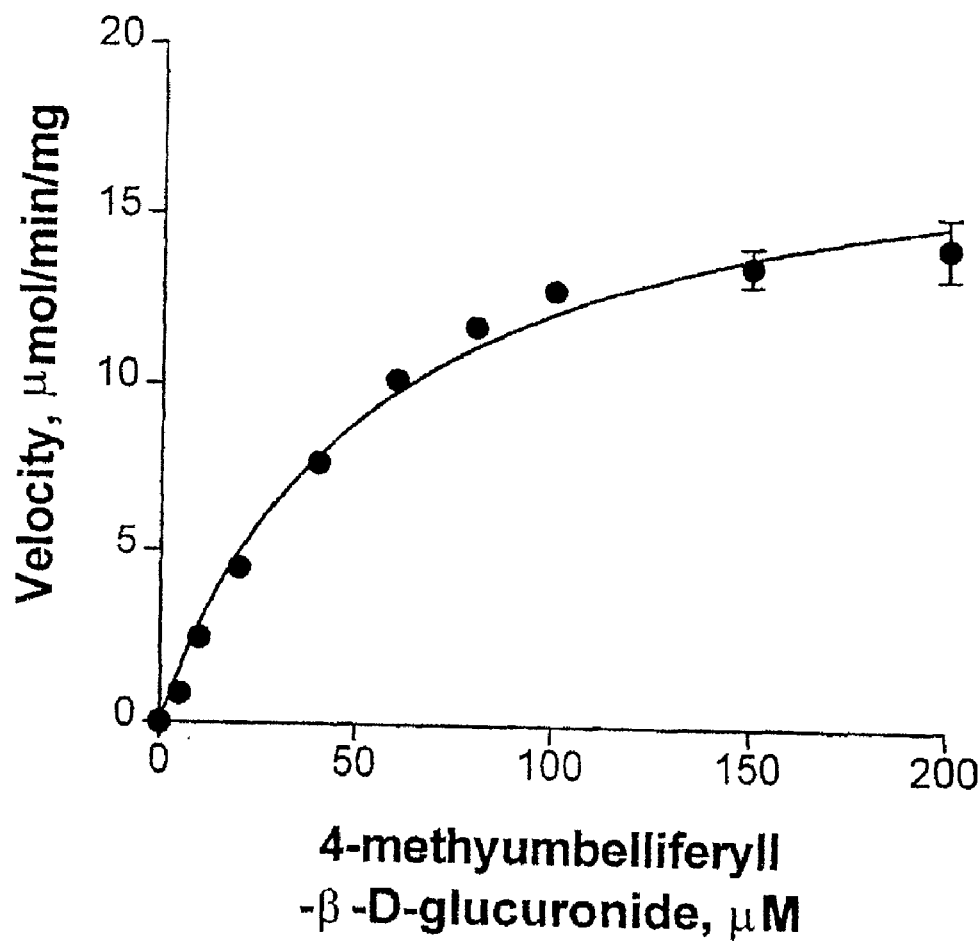

We have sought to develop an assay that can be used to demonstrate the presence of b-D-glucuronides that might be generated from different classes of UGT enzymes. An assay based on b-glucuronidase activity provides a high throughput screening method to identify structurally different b-D-glucuronides. Cleavage of 4-methylumbelliferyl b-D-glucuronide yielded the highly fluorescent compound 4-methylumbelliferone. Under linear conditions of protein concentration and incubation time, the apparent $K_m$ value for cleavage of 4-methylumbelliferyl-b-D-glucuronide was approximately 56 $\mu$M (FIG. 1A and B).

Figure 2:
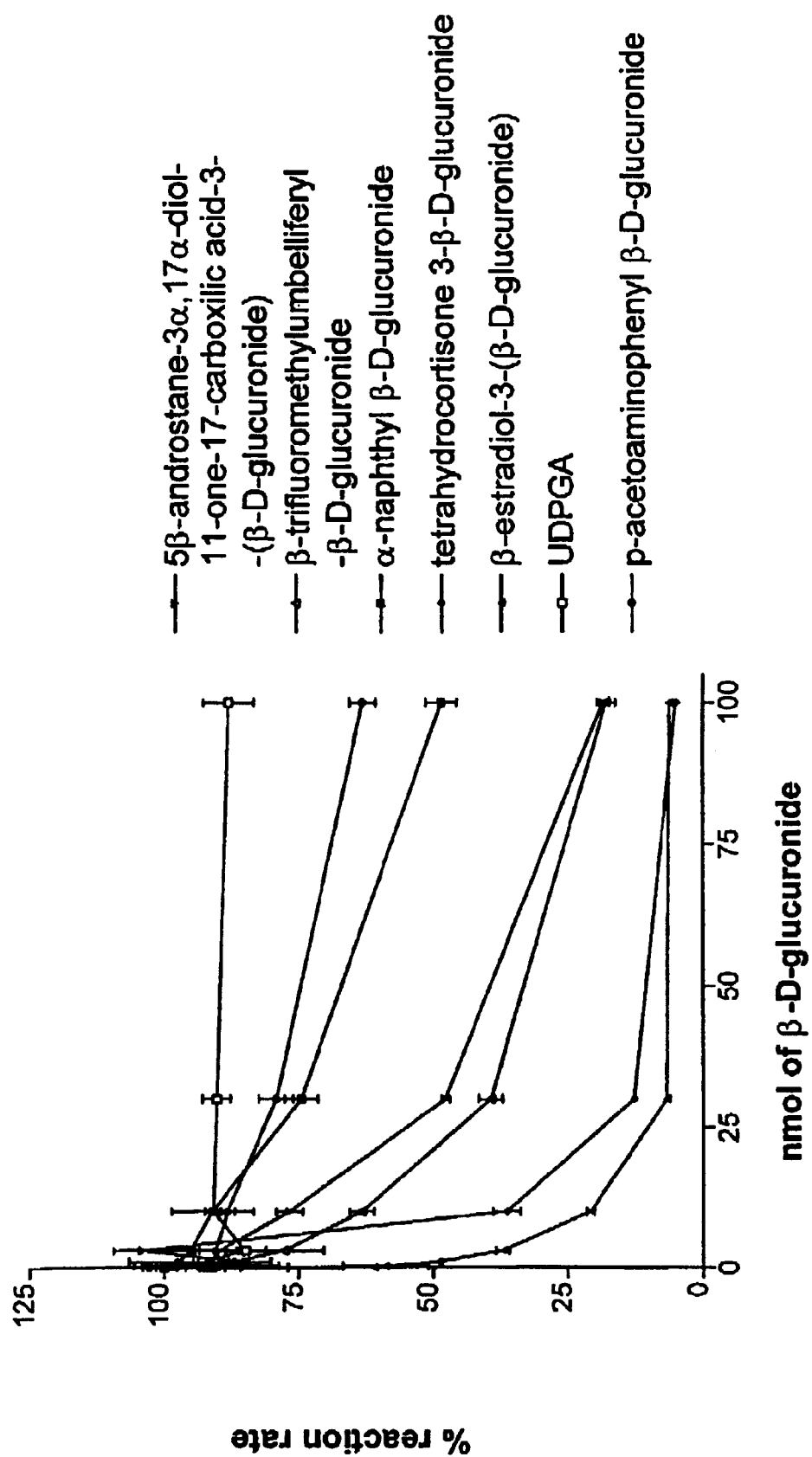
FIG. 2 Inhibition curves. Assays were performed as described in the legend to FIG. 1B with 20 □M 4-methylumbelliferyl-b-D-glucuronide and the indicated amount of competitor b-D-glucuronide. Fluorescence intensity due to 4-methylumbelliferyl-b-D-glucuronide cleavage, in the absence of a competitor was arbitrarily assigned as 100%. Competitors, α-napthyl b-D-glucuronide (■), □-trifluoromethylumbelliferyl-b-D-glucuronide (o), □-estradiol 3-□b-D-glucuronide) (▲), p-acetominophenyl b-D-glucuronide (●), 5□-androstane-3α, 17α-diol-11-one-17-carboxylic acid-3-(b-D-glucuronide) (▼) and UDPGA (∃) were dissolved in 100 mM Tris-HCl, containing 10 mM $MgCl_2$, pH 7.5. Tetrahydrocortisone 3-b-D-glucuronide (♦) was prepared in DMSO. The DMSO in reaction mixtures was 0.1% or less.

In order to show the feasibility of developing a high throughput inhibition assay, we examined the potential of a variety of structurally dissimilar commercially available b-D-glucuronides to act as inhibitors for the cleavage of 4-methylumbelliferyl-b-D-glucuronide. These b-D-glucuronides represent compounds that might potentially be formed by UGT activity e.g. phenol and steroid glucuronides. FIG. 2 shows that all of the b-glucuronides tested inhibited the production of 4-methylumbelliferone by b-glucuronidase. The potential to inhibit 4-methylumbelliferyl-b-D-glucuronide cleavage appeared to be dependent on the chemical nature of the substituted aglycone, with b-estradiol-3-(b-D-glucuronide) and α-naphthyl b-D-glucuronide showing the strongest and weakest inhibition, respectively. Uridine 5'-diphosphoglucuronic acid (UDPGA), an essential cofactor for UGTs was not an effective competitor over the range tested, probably due to the α configuration of sugar bond to UDP (Parkinson, 1996).

Figure 3A:
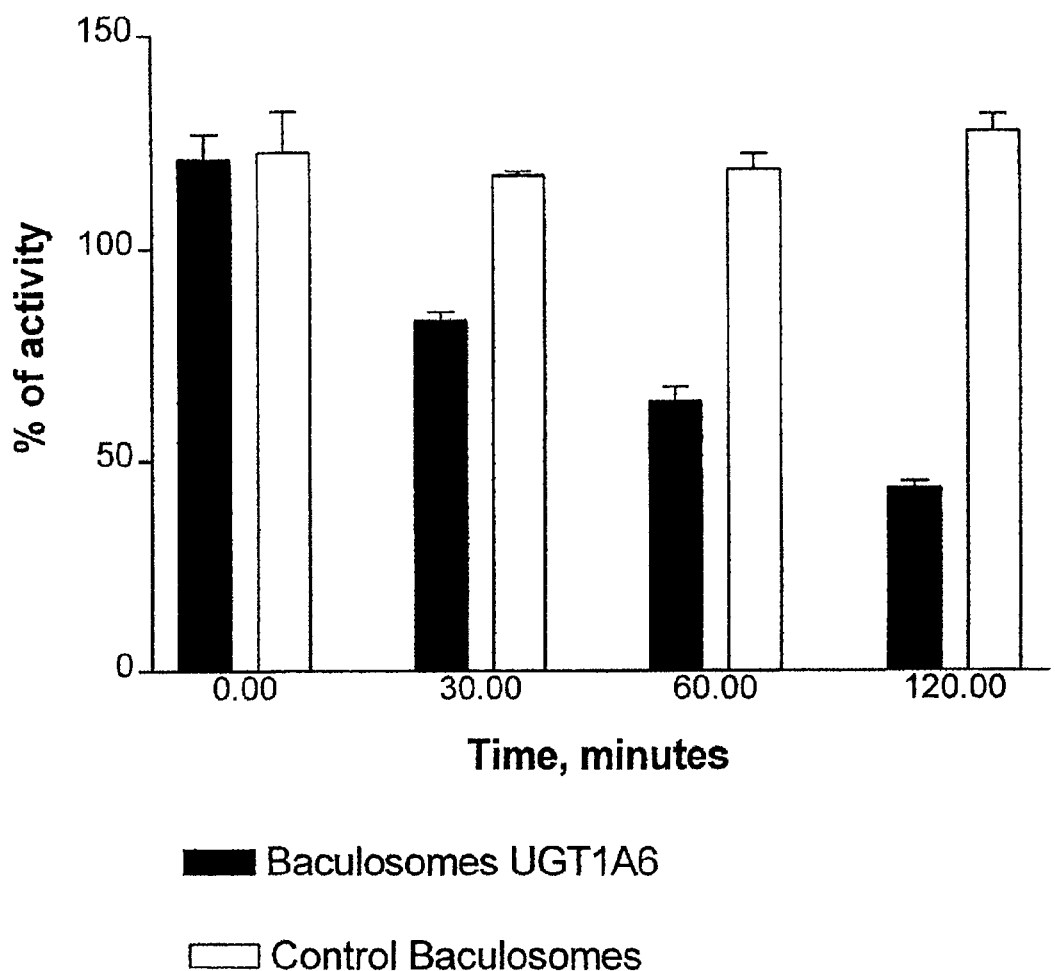
FIG. 3 Inhibition of 4-methylumbelliferyl-b-D-glucuronide cleavage by α-naphthyl glucuronide produced by recombinant UGT1A6. Both experiments were carried out as a two step procedure first an incubation was performed to generate α-naphthol glucuronide then the fluorescent cleavage assay was performed. The incubation times reflect only glucuronide generation and not the time for performing the fluorescent cleavage assay. In part A, glucuronidation assays with 0.6 mg/ml recombinant UGT1A6 (solid bars) and control (cells infected with a wild-type baculovirus, unshaded bars) insect cell extracts, were performed for the indicated times in 100 mM Tris-HCl, pH 7.4 containing 10 mM $MgCl_2$, 2 mM UDPGA, 0.6 mM α-naphthol, at 37° C. Aliquots (0.15 ml) were removed and extracted with 1.5 ml of ethyl actetate and dried down to a residue. 4-Methylumbelliferyl-b-D-glucuronide assay reagents were added directly to the residues and the reaction was performed as described in FIG. 1B for 30 minutes. Fluorescence intensity due to 4-methylumbelliferyl-b-D-glucuronide cleavage with a residue obtained from an UGT1A6 incubation in the absence of α-naphthol was arbitrarily assigned as 100%. The relative fluorescence intensity of 4-methylumbelliferyl-b-D-glucuronide cleavage assays with residues from glucuronidation incubations, which contained □-naphthol, is shown. In part B, glucuronidation assays were performed in triplicate in a 96 well plate, as in part A, for the indicated times, in a total volume of 80 □l. 10 □l each, of 100 □M 4-methylumbelliferyl-b-D-glucuronide and 1 □g/ml b-gluuronidase was then added to each assay. 4-Methylumbelliferyl-b-D-glucuronide cleavage was measured as described in the legend to FIG. 1B using a PolarStar 96-well plate analyzer (BMG, Germany) with slit widths at 20 nm and excitation and emission wavelengths of 360 and 450 nm, respectively. Fluorescence from an incubation with UGT1A6 in the absence of α-naphthol was arbitrarily assigned as 100%. The relative fluorescence intensity of assays from UGT1A6 (solid bars)

Two approaches were taken to test the feasibility of coupling the UGT-dependent production of glucuronides to inhibition of fluorescent product formation by b-D-glucuronidase. The first involved extracting the UGT reaction products and adding them to the b-D-glucuronidase fluorescence assay reagents; the second involved adding the b-D-glucuronidase reaction components directly to the quenched UGT reaction. In the first approach, α-naphthyl b-D-glucuronide was generated in an incubation with recombinant human UGT1A6 and α-naphthol. Following extraction, 4-methylumbelliferyl-b-D-glucuronide assay reagents were added to the extracted, dried reaction residues. In a separate experiment it was shown that aglycones as well as glucuronides are extracted with ethyl acetate and hence transferred to the b-gluuronidase reporter assay. FIG. 3A shows that residues from the UGT1A6 assay, but not the control microsome assay, inhibited 4-methylumbelliferyl-b-D-glucuronide cleavage. Residues from the 0 time point extractions do not appear to inhibit the 4-methylumbelliferone cleavage assay which indicated that the aglycone α-naphthol does not interfere non-specifically with this assay under these conditions. Inhibition of 4-methylumbelliferyl-b-D-glucuronide cleavage was dependent on the incubation time of the UGT1A6 assay, presumably reflecting increased □-naphthyl glucuronide accumulation. (Accumulation of b-naphthyl glucuronide in the UGT1A6 assay was independently verified in a parallel experiment using [$^{14}$C] UDPGA, data not shown.)

Figure 3B:
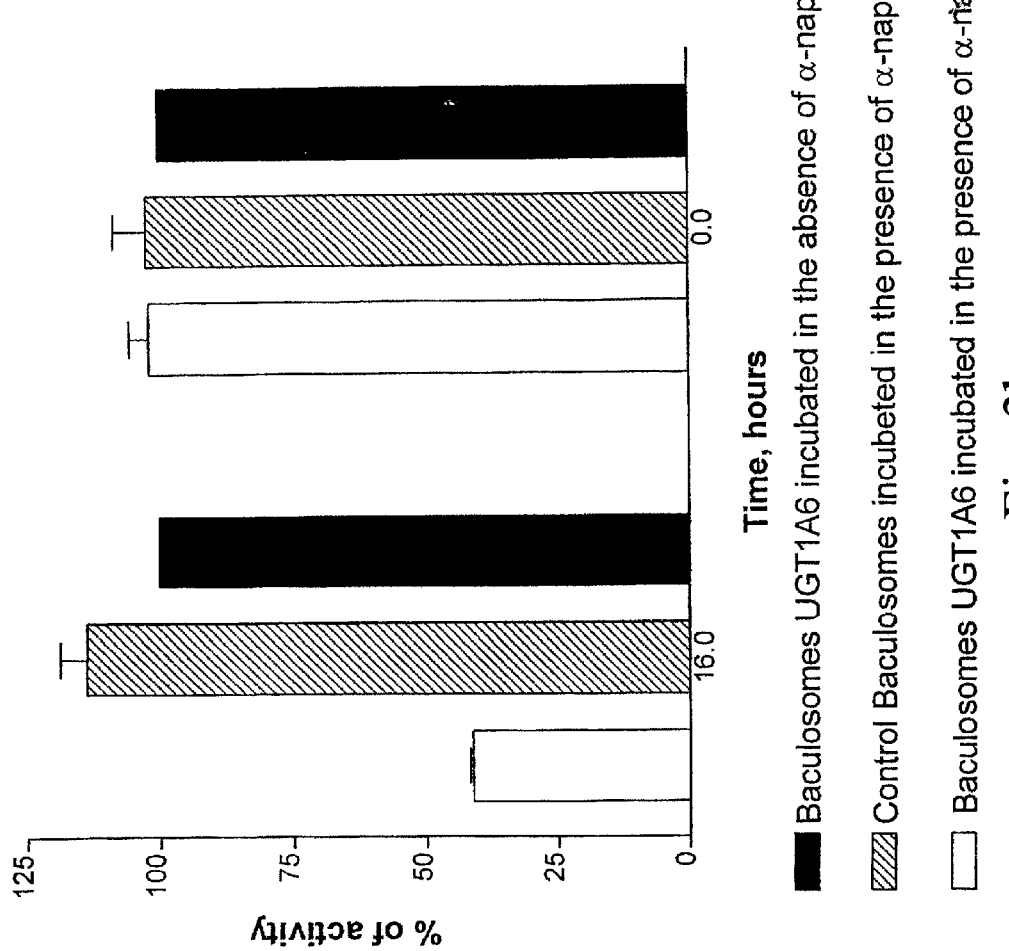

In the second approach, 4-methylumbelliferyl-b-D-glucuronide assay reagents were added directly to an b-naphthyl glucuronidation assay that was performed in a 96 well plate. FIG. 3B shows that 4-methylumbelliferyl b-D-glucuronide cleavage was 60 percent slower when added to the UGT1A6 assay compared to the control. The homogeneous format circumvented the need for extraction but required longer incubation periods with the recombinant enzyme. These results demonstrate that: i) the 4-methylumbelliferyl-b-D-glucuronide assay can be used to detect b-D-glucuronides generated in biological preparations, ii) the choice of α-naphthol b-D-glucuronide, which is a weak competitive inhibitor (FIG. 2) adds credence to this assay. More potent inhibitors such as estradiol b-D-glucuronide (FIG. 2) are likely to be more effective, iii) the assay is amenable to a high throughput format, as a two step procedure and iv) heterologous expression systems are useful for the generation of high concentrations of b-D-glucuronides, such as □-naphthyl glucuronide, which was a weak competitor (FIG. 2), in the b-D-glucuronide cleavage assay.

In summary, we have demonstrated the feasibility of using a fluorescent assay that can be adapted to a high throughput format to measure the presence of b-D-glucuronides. The assay described here uses relatively inexpensive reagents and does not require chromatographic resolution (TLC or HPLC) or radio-activity. The assay can be performed in a homogeneous format and could be easily automated. The assay will not eliminate the usefulness of other analytical procedures needed to determine the kinetic parameters of glucuronidation, but shows potential as a rapid preliminary screening method.

In addition, similar principles and procedures described here for UDP-glycosyltransferases could be applied to other important classes of phase II conjugating enzymes, e.g. sulfotransferases, N-acetyltransferases, glutathione S—transferases. For example, sulfation catalyzed by members of the sulfotransferase enzyme family, is a major metabolic pathway which modulates the biological activity of numerous endogenous and xenobiotic chemicals. Sulfate conjugates from sulfation assays would be expected to compete in a similarly designed assay that used a sulfatase to generate a fluorescent product. The following procedure can be used to demonstrate the presence of sulfated compoundes generated from multiple sources of sulfotransferases including recombinant enzymes, tissue homogenates and biological fluids. Aryl-sulfatase enzyme which is capable of cleaving a wide variety sulfated compounds can be used to design a high-throughput fluorescent assay where the products of sulfotransferase conjugation would act as competitive substrates for aryl-sulfatase cleavage of the reporter fluorescent or chromogenic substrate. The sulfatases belong to a highly conserved gene family; considerable sequence similarity exists among sulfatases of both prokaryotic and eukaryotic origins. Sulfatase of prokaryotic origin is preferable to use because of their wider substrate specificity (for example, sulfatase type IV–VIII; H1–H5 from Sigma). Possible substrates for assaying aryl-sulfatase activity include the fluorogenic ELF-97 sulfatase substrate (ELF-97 sulfate, E-6579, Molecular Probes) and the chromogenic indolyl substrates (B-8406, B-8410, Molecular Probes). ELF-97 sulfate is expected to yield a photostable yellow-green fluorescent precipitate, whereas the indolyl sulfates (B8406, B-8410) produce dark blue and magenta precipitates, respectively. The measurment of the cleavage of ELF-97 sulfate (Molecular Probes, OR) by sulfatase to the highly fluorescent compound will be possible using excitation wavelength of 345 nm and emission wavelength of 530 nm. Competitive inhibition of ELF-97 sulfatase cleavage will be used to detect the presence of sulfated metabolites of the test compound in the sulfotransferase reaction assay mixture.

We claim:

1. A process for detecting metabolite formation by an enzyme in a sample, comprising: identifying the presence of activity in a phase II conjugating enzyme involved in xenobiotic reactions by absorbance or fluorescence in a homogenous assay.

* * * * *

UNITED STATES PATENT AND TRADEMARK OFFICE
CERTIFICATE OF CORRECTION

| | | |
|---|---|---|
| PATENT NO. | : 6,319,678 B1 | Page 1 of 1 |
| APPLICATION NO. | : 09/344995 | |
| DATED | : November 20, 2001 | |
| INVENTOR(S) | : Trubetskoy et al. | |

It is certified that error appears in the above-identified patent and that said Letters Patent is hereby corrected as shown below:

On the Title page, under the heading entitled "Related U.S. Application Data," numbered paragraph item (60), Provisional application No. "60/090,727" should read --60/090,722--.

Column 1, line 7, "60/090,727" should read --60/090,722--.

Signed and Sealed this

Fourteenth Day of November, 2006

JON W. DUDAS
*Director of the United States Patent and Trademark Office*